United States Patent [19]

Koskimies et al.

[11] Patent Number: 4,816,610

[45] Date of Patent: Mar. 28, 1989

[54] PROCEDURE FOR MANUFACTURING SHORT-CHAIN LINEAR α-OLEFINES FROM ETHYLENE

[75] Inventors: Salme Koskimies, Helsinki; Leena Rantanen, Porvoo; Jouni Kivi, Espoo; Erkki Halme, Helsinki, all of Finland

[73] Assignee: Neste Oy, Finland

[21] Appl. No.: 155,238

[22] Filed: Feb. 12, 1988

[51] Int. Cl.$^4$ .............................................. C07C 2/36
[52] U.S. Cl. ................................. 585/514; 502/117; 585/512; 585/523; 585/531
[58] Field of Search ............... 585/512, 514, 523, 531; 502/117

[56] References Cited

U.S. PATENT DOCUMENTS

| | | | |
|---|---|---|---|
| 3,969,269 | 7/1976 | Count | 502/117 |
| 4,118,408 | 10/1978 | Fahey et al. | 585/514 |
| 4,315,867 | 2/1982 | Hanssle | 585/514 |
| 4,503,279 | 3/1985 | Singleton | 585/514 |

*Primary Examiner*—Asok Pal
*Attorney, Agent, or Firm*—Steinberg & Raskin

[57] ABSTRACT

The invention concerns a procedure for manufacturing short-chain linear α-olefines, in particular 1-butylene, selectively from ethylene. A nickel chelate in which the ligand is diphenyl (2-carboxymethyl) phosphine, diphenyl (2-carboxyethyl) phosphine, or an alkali metal salt of these, or an alkali metal salt of diphenyl (2-hydroxyethyl) phosphine, with or without a promoter, is used for a catalyst.

24 Claims, No Drawings

PROCEDURE FOR MANUFACTURING SHORT-CHAIN LINEAR α-OLEFINES FROM ETHYLENE

BACKGROUND OF THE INVENTION

The present invention concerns a procedure for manufacturing short-chain linear α-olefines, in particular 1-butylene, from ethylene.

These alpha-olefines have a number of special practical applications, depending on the length of the olefine chain. For instance, $C_{12}$–$C_{20}$ α-olefines are used in the manufacturing of corresponding biodegradable washing materials of sulfonate and ethoxylate types. Alcohols prepared from $C_8$–$C_{12}$ α-olefines have significant use, especially as softener alcohols. Furthermore, the use of $C_4$–$C_6$ α-olefines, particularly as a copolymer together with polyethylene, has increased in recent years, with polyethylene brands made by combination catalysis (e.g. LLDPE) displacing traditional high pressure processes (LDPE) in many areas of practical application. Moreover, t-decylene is used in continuously increasing quantities in the manufacture of poly-olefine-type synthetic lubricants.

In industrially utilized manufacturing methods, preparation of 1-butylene is effected either by performing separation of butylene isomers from the $C_4$ flow obtained on cracking, or by distilling the 1-butylene apart, e.g. from the olefine mixture produced in the manufacturing of α-olefines.

When manufacturing 1-butylene from ethylene, other oligomerizing products of ethylene are usually obtained in abundance, e.g. 2-butylene and other oligomers of varying length.

It is well-known that many catalysts can be used to oligomerize ethylene to yield olefines which have higher molecular weight. Oligomerizing is understood herein, to mean ethylene oligomerizing to become dimer, trimer, tetramer, etc., the aim being an oligomer with maximum linearity and having a double bond in alpha position.

It is a typical feature of olefine-oligomerizing reactions, that the rate of reaction and the product distribution are decisively dependent on the catalyst type, especially on the exact chemical structure of the catalyst, and on the applied reaction conditions. For instance, a drawback of well-known aluminum alkyl or aluminum alkyl/titanium halide catalysts of the "Ziegler" or "Ziegler-Natta" type, is their high reactivity and strong pyrophoric nature, although the reaction conditions (pressure, temperature) may be somewhat lower than those in the procedure of the present invention.

The previously-known catalysts of nickel phosphine type which are technically utilized in ethylene oligomerizing reactions, operate, on the other hand, in such a matter that the above-noted $C_{12}$–$C_{20}$ alpha-olefines are principally obtained as reaction products.

SUMMARY OF THE INVENTION

Accordingly, it is an object of the present invention to improve oligomerizing, especially of ethylene.

It is also an object of the present invention to improve control of oligomerizing to synthesize alpha-olefines, especially linear, short-chain alpha-olefines of lower boiling point.

It is an additional object of the prevent invention to improve selectivity and conversion in an oligomerizing reaction, especially for synthesizing 1-butylene.

It is another object of the present invention to improve isolation or purification of reaction products from oligomerizing.

These and other objects are attained by the present invention which is directed to a method of producing short-chain linear alpha-olefines from ethylene, which comprises subjecting ethylene to oligomerization in the presence of a nickel chelate catalyst having as a ligand, diphenyl(2-carboxymethyl)phosphine, or diphenyl(2-carboxyethyl)phosphine, or alkali metal salts of diphenyl(2-carboxymethyl)phosphine or diphenyl(2-carboxyethyl)phosphine, or an alkali metal salt of diphenyl(2-hydroxyethyl)phosphine. The oligomerization may be additionally carried out in the presence of a promoter forming part of the catalyst.

The present invention is also directed to a method of preparing the above-noted catalyst for synthesizing the short-chain linear alpha-olefines from ethylene.

Accordingly, in contrast to the above-noted catalyst and procedures, the present invention concerns a procedure which allows the ethylene oligomerizing reaction to be controlled so that the products which are obtained are specifically linear alpha-olefines with lower boiling point, used as starting substances for plastics and/or synthetic lubricants.

By the procedure in accordance with the present invention, 1-butylene can be especially selectively manufactured, with high conversion (60–70%). The catalyst employed in the dimerizing procedure differs from any other known nickel phosphine catalyst used in oligomerizing with respect to the promoters used to modify the catalyst.

The procedure constituting the pressure invention also differs from other nickel phosphine-catalytic procedure, especially in that the catalysts which are utilized have been prepared either by synthesizing a new phosphine ligand and/or changing the reactivity of the previously-known phosphine catalyst e.g. with the air of amines in a manner causing the reaction to be directed towards short-chain linear alpha-olefines.

The procedure of the present invention for manufacturing short-chain, linear alpha-olefines, in particular 1-butylene, is therefore principally characterized by using a nickel chelate in which the phosphine ligand is diphenyl(2-carboxymethyl)phosphine, diphenyl(2-carboxyethyl)phosphine, the alkali metal salts of these or an alkali metal salt of diphenyl(2-hydroxyethyl)phosphine, with or without a promoter, for a catalyst.

Diphenyl(2-carboxyethyl)phosphine is also known under the names (beta-carboxyethyl)diphenylphosphine and diphenylphosphinopropionic acid, while diphenyl(2-carboxymethyl)phosphine is also known under the name diphenylphosphinoacetic acid.

It is thus understood that in the present procedure, nickel diphenylphosphinopropionic acid chelate or nickel diphenylphosphinoacetic acid chelate, or nickel diphenyl(2-hydroxyethyl)phosphino chelate is used for a catalyst, together with a promoter if required. An amine or acetic acid derivative then serves as the promoter.

The alkali metal salts of diphenylphosphinoacetic acid or propionic acid can be prepared, e.g., by treating these acids with an alkali metal hydroxide, with an oxide, or with a free metal. For diphenyl(2-hydroxyethyl)phosphine ligand, it is simplest to use a straight alkali metal salt prepared by reaction between triphenylphosphine, potassium, and 2-chloroethanol.

Particular significance from the viewpoint of the present invention, follows from the synergy of the structures of the phosphone ligand molecule and the amine. Amine modification not only changes reactivity of the catalyst so that the formation of linear alpha-olefines having a longer chain is reduced, but also significantly increases the total conversion of ethylene to alpha-olefine and thus also acts as a promoter.

The use of amine and/or acetate promoters in the procedure of the invention together with nickel diphenylphosphinopropionic acid chelate or nickel diphenylphosphinoacetic acid chelate or nickel diphenyl(2-hydroxyethyl)phosphine chelate significantly increases the conversion of ethylene particularly to butylene, and also increases the 1-butylene selectivity. It is particularly significant in this connection, that with increasing conversion, especially when amine promoters are used, proportion of longer-chain olefines does not increase in the same proportion. This promoter accelerates, above all, the dimerizing reaction, and correspondingly inhibits the formation of longer-chain olefines produces from ethylene in oligomerization.

DESCRIPTION OF THE PREFERRED EMBODIMENTS

The procedure of the present invention and the advantageous embodiments thereof will be presented in greater detail below.

The present invention especially concerns those procedures in which nickel diphenylphosphinopropionic acid chelate, nickel diphenylphosphinoacetic acid chelate, or nickel diphenyl(2-hydroxyethyl)phosphine chelate together with a promoter, are dissolved at 10° to 50° C. in a polar organic solvent preferably containing oxygen, nitrogen or sulphur atoms (polyols, glycols, glycolethers, ethers, amides, cyano compounds, sulphonyl derivatives, etc.). Solvents which are suitable in view of the reaction, also include non-polar organic solvents such as aliphatic and aromatic hydrocarbons and the chlorine, bromine or fluorine derivatives thereof.

The recommendable ethylene pressure during reaction is about 0.069 to 35 MPa, preferably about 2.8 to 10 MPa. A suitable reaction temperature is about 30°–200° C., preferably about 50° to 200° C., more preferably about 60° to 130° C., with reaction time preferably being about 0.5 to 50 hours, more preferably about 3 to 30 hours. The molar proportions regarding nickel salt- :ligand:reducing agent; and promoter which are recommended, are preferably about 1–5:1:1–10:1–5, more preferably about 1–5:1:2–10:1–5, even more preferably about 1.5–3:1:3–6:1–7, and most preferably 1.5–3:1:3–6:- 1–2.

For the above nickel salt or derivative, a nickel halide, e.g. nickel chloride, bromide, or iodide may be used. However, it is especially favorable in view of the reaction to use nickel acetate, of which the acetate part then also serves as a reaction promoter.

Activation of the reaction is accomplished with the aid of a reducing agent. Various borohydride salts, preferably alkali metal borohydrides, are appropriate for such use.

Suitable compounds for use as amine-type promoters in the reaction include primary, secondary, and tertiary amines, and aromatic, aliphatic and cyclic monoamines and diamines, e.g. butylamine, triethylamine, N,N,N',N'-tetramethylethyldiamine, N,N-dimethylpiperazine, etc.

Regarding the diphenylphosphinopropionic acid ligand or the diphenylphosphinoacetic acid ligand, these ligands may be used as is, or the corresponding alkali salts may be prepared, e.g. by treating the ligands with an alkali metal hydroxide, an oxide, or a free metal. For diphenyl(2-hydroxyethyl)phosphine ligand, it is simplest to use an alkali metal salt directly prepared by means of a reaction between triphenyl phosphine, potassium, and 2-chloroethanol.

Therefore, it is fundamental in the procedure of the present invention, and also differing from other methods previously known, that by using for a catalyst, nickel phosphinoacetic acid chelate together with an amine derivative, or nickel phosphinopropionic acid chelate or nickel(2-hydroxyethyl)phosphine chelate either as such or in combination with an amine derivative, ethylene can be oligomerized into short-chain linear α-olefines, and that the use or an amine derivative not only inhibits the formation of longer-chain α-olefines but also acts an an efficient promoter, increasing the ethylene conversion.

Another advantage gained with the aid of the procedure of the present invention, is that purification of the 1-butylene from polymerizing quality to required level can be carried out with ease, in the case of a reaction product prepared by the procedure of the invention (Table 3), by distillation. This is possible because isobutylene, which is harmful from the viewpoint of polymerization, is not formed at all, while 2-butylene is inert in any coordination-catalytic polymerizing system. This means that difficult separation of butylene isomers is avoided.

The present invention will be further described in greater detail below, by way of the following examples:

EXAMPLES 1–3

Catalysts were prepared in a pressurized reactor in a nitrogen atmosphere, by adding diphenylphosphinopropionic acid, nickel chloride, and 2N aqueous KOH solution to 125 ml of butane diol. The reactor was pressurized with ethylene to 3.45 MPa and the mix was agitated during 15 min at 20°–40° C. Reducing agent solution (NaBH$_4$ dissolved in 5 ml of N,N-dimethylacetamide) was added in an N$_2$ atmosphere and the pressure was raised with ethylene to 5.2 MPa. After 15 min. mixing, the temperature in the reactor was raised to 100° C. and thereafter kept constant as long as there was reaction. The reactor was cooled, and the gases, liquids and solids that had been formed were analyzed. The quantities of starting materials and products, and the reacting conditions, are stated in Table 1.

EXAMPLES 4–5

The same experimental arrangements were conducted as in Examples 1–3, with the exception that nickel acetate was used for starting material instead of nickel chloride, in preparing the catalyst. The conditions in the experiment, and the product quantity, are stated in Table 1. The product structure analysis obtained in Example 5 is given in Table 3.

EXAMPLES 6–7

Arrangements for the experiment were made as in Examples 1–3, with the exception that, at the catalyst adding stage, an amine derivative (n-butylamine or N,N-dimethylpiperazine) was added to the catalyst solution. The results are given in Table 1.

EXAMPLES 8-9

Arrangements were made as in Examples 1-3, with the exception that nickel acetate was used instead of nickel chloride and N,N-dimethylpiperazine was added for extra promoter. The results are given in Table I.

EXAMPLES 10-15

Arrangements were made as in Examples 1-3, with the exception that calcium salt of diphenyl(2-hydroxyethyl)phosphine was used for ligand as such, without extra KOH addition. Promoters, acetate and/or amine(N,N-dimethylpiperazine) were similarly added as in Examples 4-9. The results are given in Table 2.

EXAMPLE 16

The experiment was carried out as in Example 1, with a temperature of 90°-100° C. for reaction temperature. The results are given in Table 4.

EXAMPLES 22-25

Arrangements were made as in Examples 1 and 17, with the exception that diphenylphosphinopropionic acid was used for ligand, chloride for nickel salt, and either butylamine (Example 23) or N,N-dimethylpiperazine (Examples 24-25) was used for amide. The reaction temperature which was applied was 90°-100° C. The results are given in Table 4.

Example numbers 1-10 at the top of Table 4 correspond to Examples 16-25 respectively.

The exact hydrocarbon structure distribution found for all products prepared in Examples 16-25 is stated in Table 5.

The preceding description of the present invention is merely exemplary and is not intended to limit the scope thereof in any way.

TABLE 1

OLIGOMERIZATION OF ETHYLENE WITH THE AID OF (PROPIONIC ACID) CHELATE[a]

| | EXAMPLE | | | | | | | | |
|---|---|---|---|---|---|---|---|---|---|
| | 1 | 2 | 3 | 4 | 5 | 6 | 7 | 8 | 9 |
| Starting materials: | | | | | | | | | |
| Phosphine (mmol)[d] | 0.5 | 0.5 | 1.0 | 0.5 | 0.5 | 0.5 | 0.5 | 0.5 | 0.5 |
| Ni II (mmol) | | | | | | | | | |
| chloride | 1.0 | 1.1 | 2.0 | — | — | 1.1 | — | — | |
| acetate | — | — | — | 1.0 | 1.1 | — | — | 1.0 | 1.0 |
| $NaBH_4$ (mmol) | 2.8 | 2.8 | 2.8 | 2.8 | 2.8 | 2.8 | 2.0 | 2.0 | 2.0 |
| amine (mmol) | — | — | — | — | — | 0.5[b] | 0.5[c] | 0.5[c] | 0.5[c] |
| ethylene (g) | 55.0 | 68.7 | 76.3 | 65.4 | 50.1 | 55.0 | 49.0 | 51.3 | 49.6 |
| Reaction time (h) | 4.5 | 23 | 4.5 | 17.5 | 22 | 6.5 | 20 | 4 | 22 |
| Products (% b.w.) | | | | | | | | | |
| Butylenes | 79.50 | 86.72 | 93.50 | 87.35 | 91.40 | 90.22 | 88.92 | 84.84 | 88.68 |
| Hexylenes | 9.61 | 4.64 | 3.05 | 10.32 | 6.91 | 7.21 | 5.50 | 8.42 | 7.40 |
| Octylenes | 3.32 | 2.46 | 0.15 | 1.86 | 0.97 | 1.52 | 1.37 | 3.83 | 2.29 |
| Decylenes | 2.75 | 1.09 | — | 0.38 | 0.29 | 0.54 | 0.58 | 1.50 | 0.82 |
| Dodecylenes | 1.69 | 0.57 | — | 0.07 | 0.15 | 0.26 | 0.32 | 0.70 | 0.35 |
| Tetradecylenes | 1.13 | 0.28 | — | — | 0.09 | 0.11 | 0.17 | 0.32 | 0.19 |
| Hexadecylenes | 0.77 | 0.19 | — | — | 0.06 | 0.06 | 0.09 | 0.17 | 0.11 |
| +18 hydrocarbons | 1.20 | 4.03 | 3.30 | — | 0.12 | 0.08 | 3.05 | 0.22 | 0.16 |
| Ethylene conv. (%) | 27.0 | 30.8 | 26.7 | 69.0 | 67.5 | 66.1 | 70.21 | 80.5 | 74.3 |
| Butylene select. (%) | 75.7 | 86.4 | 93.1 | 87.3 | 91.4 | 86.7 | 88.8 | 84.7 | 88.6 |
| 1-butylene (in % of butylenes) | 98.2 | 93.5 | 94.0 | 91.1 | 95.6 | 97.6 | 92.0 | 86.4 | 93.0 |

[a] t = 100° C., p = 5.2 MPa
[b] Butylamine
[c] N,N—dimethylpiperazine
[d] Potassium salt of diphenylphosphinopropionic acid the exception that diphenylphosphinoacetic acid was used instead of diphenylphosphinopropionic acid, and a temperature between 70° and 75° C. was used instead of 100° C. The quantities of starting materials and products, along with the reaction conditions, are listed in Table 4.

EXAMPLE 17

The experiment was similarly carried out as in Example 16, with the exception that 2 N,N-dimethylpiperazine was also added to 125 ml butane diol. The results are given in Table 4.

EXAMPLES 18-21

Experimental arrangements were conducted as in Examples 1 and 17, with the exception that potassium salt of diphenyl(2-hydroxyethyl)phosphine was used for ligand, chloride or acetate for nickel salt, and N,N-dimethylpiperazine for amine (Examples 19 and 21), and

TABLE 2

Oligomerization of ethylene with the aid of dihenyl(2-hydroxyethyl)phosphine

| | Example | | | | | |
|---|---|---|---|---|---|---|
| | 10 | 11 | 12 | 13 | 14 | 15 |
| Starting materials | | | | | | |
| Phosphine[a] (mmol) | 0.5 | 0.5 | 0.5 | 0.5 | 0.5 | 0.5 |
| Ni (II) (mmol) | | | | | | |
| chloride | 1.0 | 1.0 | 1.0 | 1.0 | — | — |
| acetate | — | — | — | — | 1.0 | 1.0 |
| $NaBH_4$ (mmol) | 2.0 | 2.0 | 2.0 | 2.0 | 2.0 | 2.0 |
| Amine (mmol) | — | 0.5[b] | — | 0.5[b] | — | 0.5[b] |
| Ethylene (g) | 70.4 | 50.6 | 64.6 | 50.3 | 54.6 | 54.6 |
| Reaction time (h) | 6.5 | 6.0 | 17 | 18 | 19 | 17 |
| Products (% b.w.) | | | | | | |
| Butylenes | 72.76 | 84.43 | 84.24 | 83.73 | 81.99 | 92.75 |
| Hexylenes | 13.51 | 9.90 | 9.05 | 9.68 | 12.59 | 5.88 |
| Octylenes | 9.79 | 4.30 | 4.99 | 5.02 | 4.08 | 1.10 |
| Decylenes | 2.61 | 1.00 | 1.04 | 1.17 | 0.92 | 0.19 |
| Dodecylenes | 0.84 | 0.27 | 0.35 | 0.26 | 0.22 | 0.05 |
| Tetradecylenes | 0.28 | 0.07 | 0.14 | 0.07 | 0.07 | — |
| Hexadecylenes | 0.12 | — | 0.08 | — | — | — |
| +18 hydrocarbons | 0.09 | — | 0.10 | — | 0.10 | — |

TABLE 2-continued

Oligomerization of ethylene with the aid of dihenyl(2-hydroxyethyl)phosphine

| | Example | | | | | |
|---|---|---|---|---|---|---|
| | 10 | 11 | 12 | 13 | 14 | 15 |
| Ethylene conversion (%) | 48.8 | 99.3 | 75.8 | 83.1 | 75.4 | 76.4 |
| Butylene selectivity (%) | 72.6 | 84.3 | 84.2 | 83.6 | 81.9 | 92.6 |
| 1-butylene (% of butylenes) | 95.0 | 97.0 | 94.5 | 89.0 | 88.8 | 89.8 |

(a)Potassium salt of (2-hydroxyethyl)phosphine
(b)N,N—dimethylpiperazine
(c)t = 100° C.; p = 5.2 MPa

TABLE 3

Typical product structure distribution in a gas sample as obtained in the ethylene oligomerizing reaction (Example 5).

| | | % by weight |
|---|---|---|
| 1 | Ethylene | 33.1 |
| 7 | 1-butylene | 60.1 |
| 9 | n-butane | 0.12 |
| 10 | Tr-2-butylene | 1.2 |
| 12 | Cis-2-butylene | 1.5 |
| 18 | 2-Et-1-butylene | 0.4 |
| 33 | 3-Me-1-pentene | 0.02 |
| 43 | 1-hexylene | 3.0 |
| 45 | Tr-3-hexylene | 0.1 |
| 46 | Cis-3-hexylene | 0.1 |
| 105 | C8H16 olef. | 0.04 |
| 111 | 1-octylene | 0.1 |

TABLE 4

OLIGOMERIZATION OF ETHYLENE

| | EXAMPLE | | | | | | | | | |
|---|---|---|---|---|---|---|---|---|---|---|
| | 1(f) | 2(f) | 3(g) | 4(g) | 5(g) | 6(g) | 7(g) | 8(g) | 9(g) | 10(g) |
| Starting materials: | | | | | | | | | | |
| Phosphine (mmol) | 0.5(a) | 0.5(a) | 0.5(c) | 0.5(c) | 0.5(c) | 0.05(c) | 0.5(d) | 0.5(d) | 0.5(d) | 0.5(d) |
| Ni (II) (mmol) | | | | | | | | | | |
| Chloride | 1.0 | 1.0 | 1.0 | 1.0 | — | — | 1.0 | 1.0 | 1.1 | 1.0 |
| Acetate | — | — | — | — | 1.0 | 1.0 | | | | |
| NaBH4 (mmol) | 2.8 | 2.8 | 2.0 | 2.0 | 2.0 | 2.0 | 2.8 | 2.8 | 2.0 | 2.0 |
| Amine (mmol) | — | 0.5(b) | — | 0.5(b) | — | 0.5(b) | — | 0.5(e) | 0.5(b) | 0.5(b) |
| Ethylene (g) | 245.2 | 272.1 | 70.4 | 50.4 | 54.6 | 54.6 | 55.0 | 55.0 | 51.9 | 49.6 |
| Reaction time (h) | 5 | 6 | 6.5 | 18 | 19 | 17 | 4.5 | 6.5 | 20 | 22 |
| Products (%): | | | | | | | | | | |
| Butylenes | 22.1 | 40.8 | 72.7 | 83.7 | 82.0 | 92.6 | 79.0 | 90.1 | 84.7 | 88.8 |
| Hexylenes | 18.9 | 19.0 | 13.2 | 9.7 | 12.6 | 5.2 | 9.8 | 7.2 | 5.2 | 7.4 |
| Octylenes | 24.1 | 18.4 | 9.7 | 5.0 | 4.1 | 1.1 | 3.5 | 1.5 | 1.3 | 2.3 |
| Decylenes | 14.0 | 8.8 | 2.5 | 1.2 | 0.9 | 0.2 | 2.8 | 0.3 | 0.6 | 0.8 |
| Dodecylenes | 8.0 | 5.0 | 0.8 | 0.3 | 0.2 | 0.05 | 1.7 | 0.1 | 0.3 | 0.4 |
| Tetradecylenes | 4.7 | 3.0 | 0.3 | 0.05 | 0.1 | — | 1.2 | 0.05 | 0.2 | 0.2 |
| Hexadecylenes | 3.0 | 1.8 | 0.1 | — | 0.05 | — | 0.8 | — | 0.1 | 0.1 |
| Octadecylenes | 1.8 | 1.1 | 0.05 | — | — | — | 0.5 | — | 0.05 | 0.05 |
| Eicosenes | 1.2 | 0.7 | — | — | — | — | 0.3 | — | — | — |
| +20 hydrocarbons | 2.1 | 1.8 | — | — | — | — | 0.4 | — | 2.8 | 0.1 |
| Ethylene conv. (%) | 54.3 | 64.4 | 45.8 | 83.1 | 75.4 | 76.4 | 27.0 | 66.1 | 70.2 | 74.3 |

(a)Potassium salt of diphenylphosphinoacetic acid
(b)N,N—dimethylpiperazine
(c)Potassium salt of diphenyl(2-hydroxyethyl)phosphine
(d)Potassium salt of diphenylphosphinopropionic acid
(e)Butylamine
(f)t = 70-75°, p = 750 psi
(g)t = 90-100°, p = 750 psi

TABLE 5

Typical product structure distribution in gas sample as obtained in the ethylene oligomerizing reaction.

| | | % by weight |
|---|---|---|
| 2 | Ethylene | 26.6 |
| 3 | Ethane | 0.4 |
| 7 | i + 1-butylene | 63.9 |
| 9 | n-butane | 0.04 |
| 10 | Tr-2-butylene | 2.1 |
| 12 | Cis-2-butylene | 2.7 |
| 18 | 2-Et-1-butylene | 0.6 |
| 33 | 3-Me-1-pentene | 0.03 |
| 43 | 1-hexylene | 2.9 |
| 45 | Tr-3-hexylene | 0.1 |
| 46 | Cis-3-hexylene | 0.1 |
| 48 | Tr-2-hexylene | 0.1 |
| 52 | Cis-2-hexylene | 0.2 |
| 111 | 1-octylene | 0.03 |

What is claimed is:

1. Method of producing short-chain linear olefines from ethylene, which comprises subjecting ethylene to oligomerization in the presence of a nickel chelate catalyst having as a ligand, an alkali metal salt of diphenyl(2-hydroxyethyl)phosphine.

2. The method of claim 1, additionally comprising carrying out said oligomerization in the presence of a promoter forming part of said catalyst.

3. The method of claim 2, wherein said promoter is an amine or acetate derivative.

4. The method of claim 1, additionally comprising dissolving said catalyst in an organic solvent at about 10°–50° C.

5. The method of claim 1, additionally comprising dissolving said promoter, together with said catalyst, in an organic solvent at about 10°–50° C.

6. The method of claim 1, additionally comprising carrying out said oligomerization at a temperature of about 30°–200° C.

7. The method of claim 6, wherein said temperature is about 50°–200° C.

8. The method of claim 7, wherein said temperature is about 60° to 130° C.

9. The method of claim 1, additionally comprising carrying out said oligomerization at a pressure of about 0.069–35 MPa.

10. The method of claim 9, wherein said pressure is about 2.8–10 MPa.

11. The method of claim 1, additionally comprising carrying out said oligomerization for a reaction time of about 0.5–50 hours.

12. The method of claim 11, wherein said time is about 3–30 hours.

13. The method of claim 2, additionally comprising activating said oligomerization with the aid of a reducing agent.

14. The method of claim 13, wherein said reducing agent is a borohydride salt.

15. The method of claim 14, wherein said borohydride salt is an alkali metal borohydride.

16. The method of claim 13, additionally comprising carrying out said oligomerization with a molar ratio of nickel salt:ligand:reducing agent:promoter of about 1–5:1:1–10:1–5.

17. The method of claim 16, wherein said molar ratio is about 1–5:1:2–10:1–5.

18. The method of claim 13, additionally comprising carrying out said oligomerization with a molar ratio of nickel salt:ligand:reducing agent:promoter of about 1.5–3:1:3–6:1–7.

19. The method of claim 18, wherein said molar ratio is about 1.5–3:1:3–6:1–2.

20. The method of claim 1, additionally comprising separating and purifying 1-butylene synthesized during said oligomerization by distillation.

21. The method of claim 3, wherein said amine includes butylamine, triethylamine, N,N,N',N'-tetramethylethylamine, and N,N-dimethylpiperazine.

22. Method of preparing a catalyst for synthesizing short-chain linear alpha-olefines from ethylene, which comprises forming a nickel chelate with a phosphate ligand which is an alkali metal salt of diphenyl(2-hydroxyethyl)phosphine.

23. The method of claim 22, additionally comprising preparing the catalyst with a nickel derivative which is a nickel halide or nickel acetate, said acetate part of which additionally serving as a promoter of said synthesizing.

24. The method of claim 22, additionally comprising preparing said alkali metal salt of diphenyl(2-hydroxyethyl)phosphine by reacting triphenylphosphine, potassium, and 2-chloroethanol.

* * * * *